(12) United States Patent
Banfi et al.

(10) Patent No.: US 7,858,779 B2
(45) Date of Patent: Dec. 28, 2010

(54) PROCESS FOR PREPARING OXCARBAZEPINE

(75) Inventors: Aldo Banfi, Milan (IT); Deborah Bollini, Romano die Lombardia (IT); Maurizio Serra, Cassano d'adda (IT); Gianluca Di Lernia, Milan (IT)

(73) Assignee: Archimica S.r.l., Milan (IT)

( * ) Notice: Subject to any disclaimer, the term of this patent is extended or adjusted under 35 U.S.C. 154(b) by 1149 days.

(21) Appl. No.: 10/580,145

(22) PCT Filed: Feb. 21, 2005

(86) PCT No.: PCT/IB2005/000452

§ 371 (c)(1),
(2), (4) Date: May 18, 2006

(87) PCT Pub. No.: WO2005/092862

PCT Pub. Date: Oct. 6, 2005

(65) Prior Publication Data

US 2007/0149507 A1   Jun. 28, 2007

(30) Foreign Application Priority Data

Mar. 9, 2004   (IT)   .......................... MI2004A0452

(51) Int. Cl.
C07D 223/22   (2006.01)
C07D 223/28   (2006.01)
(52) U.S. Cl. .................................................... 540/589
(58) Field of Classification Search ................. 540/589
See application file for complete search history.

(56) References Cited

U.S. PATENT DOCUMENTS

| 3,642,775 | A | 2/1972 | Schindler |
| 5,808,058 | A | 9/1998 | Milanese |
| 6,340,760 | B1 | 1/2002 | Bellani et al. |
| 6,399,822 | B1 | 6/2002 | Eckert et al. |
| 2003/0032800 | A1 | 2/2003 | Fuenfschilling |
| 2003/0105076 | A1 | 6/2003 | Ansari |
| 2007/0032647 | A1* | 2/2007 | Parenky et al. ............... 540/589 |

FOREIGN PATENT DOCUMENTS

IT   1318371   8/2003

OTHER PUBLICATIONS

English language of Hungarian Patent No. HU63389, Aug. 30, 1993, Ferenc Haasz, et al., Procedure prepn. of 5-carbamoyl-10-oxo-10,11,dihydro-5H-dibenz[b,f]azepine.
Heiner, E. et al., "Triphosgene, a Crystalline Phosgene Substitute", Angew. Chem. Int. Ed. Engl, 26 (1987), No. 9.(Abstract and p. 895).
E. Jon Jacobsen et al.; *Piperazine Imidazo[1,5-a] quinoxaline Ureas as High-Affinity GABA$_A$ Ligands of Dual Functionality*[1] Journal of Medicinal Chemistry, 1999, vol. 42. No. 7 p. 1123-1144.
Lucia Pasquato et al.; *Conversion of Bis(trichloromethyl) Carbonate to Phosgene and Reactivity of Triphosgene, Diphosgene, and Phosgenee with methanol*[1] Journal of Organic Chemistry, 2000, vol. 65. p. 8224-8228.

* cited by examiner

*Primary Examiner*—Brenda L Coleman
(74) *Attorney, Agent, or Firm*—ProPat, L.L.C.

(57) ABSTRACT

Process for preparing oxcarbazepine according to the steps of chlorocarbonylating (a), ammonolysis (b), and deprotecting (c).

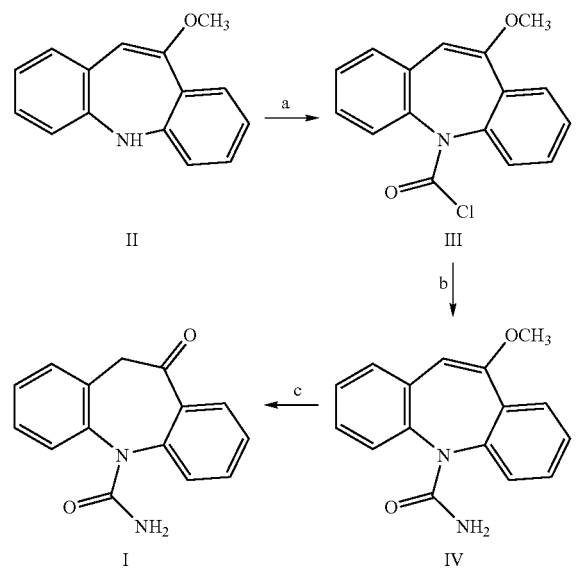

The invention is characterized by the use of triphosgene as chlorocarbonylating agent in step a).

13 Claims, No Drawings

PROCESS FOR PREPARING OXCARBAZEPINE

This application is a national stage entry under 35 U.S.C. §371 of PCT/IB05/00452, filed Feb. 21, 2005.

The present invention relates to a novel process for preparing oxcarbazepine, which is particularly advantageous from an industrial point of view, characterized by the use of triphosgene as chlorocarbonylating agent.

PRIOR ART

Oxcarbazepine (Merck Index, 1996, No. 7063) of formula

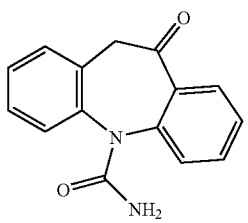

(I)

is a known anticonvulsivant agent, which was described for the first time in German patent DE 2 011 087 (Ciba-Geigy).

Various processes are reported in the literature for preparing oxcarbazepine, these processes essentially involving the introduction of the carboxamide function onto the nitrogen in position 5 by means of carbamoylation with cyanates, for example in WO 01/56992, EP 1 302 464, IT 000MI0311 and WO 96/21649, or, as illustrated in Scheme 1 below and in U.S. Pat. No. 3,642,775 and HU63389, by chlorocarbonylation (a) followed by ammonolysis (b) and final hydrolysis (c):

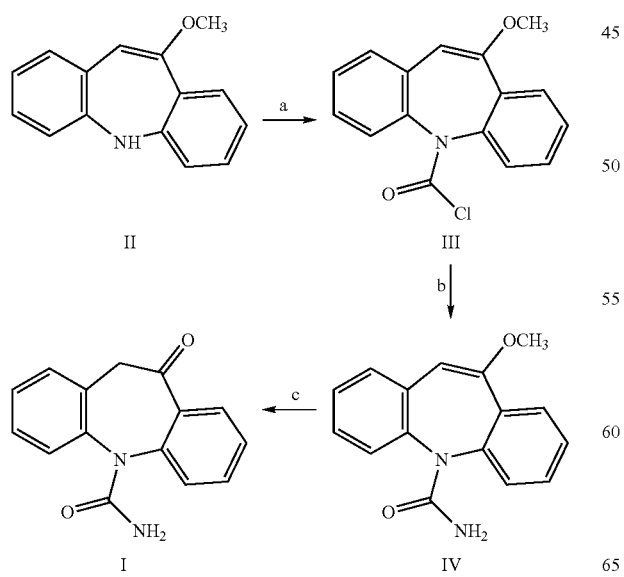

SCHEME 1

In particular, U.S. Pat. No. 3,642,775 describes a chlorocarbonylation reaction (a) performed with phosgene, in toluene at 95° C., with a yield of 77% of compound II after crystallization from ethanol, and subsequent ammonolysis (b) with ammonia gas in ethanol, with a yield of 73% of compound IV, also calculated after crystallization from ethanol (56% overall yield for the two steps a and b).

The final deprotection of compound IV to give oxcarbazepine (c) is performed by refluxing with 2N hydrochloric acid, in a yield of 80%, after crystallization from ethanol. The overall yield for this process (II→III→IV→I) is equal to about 45%.

However, the use of phosgene as chlorocarbonylating agent in this synthetic route represents a considerable drawback on account of its high toxicity and corrosiveness.

From the abstract in Chemical Abstracts of Hungarian patent HU63389, the same sequence as that of Scheme 1 is performed, but with diphosgene in refluxing toluene (a), subsequent ammonolysis of the intermediate III, which is not isolated, with ammonia gas (b) (yield for steps a) and b) equal to 58.9%) and, finally, hydrolysis of the intermediate IV with 2M HCl, in a yield equal to 73.5%. In this case, the overall yield for the process, calculated on the basis of the partial values reported in the abstract, is equal to 43.3%.

We have now found, surprisingly, an industrially acceptable process for preparing oxcarbazepine, which, without using corrosive reagents such as phosgene, makes it possible to obtain the desired product while significantly increasing the overall yields.

DESCRIPTION OF THE INVENTION

One subject of the present invention is thus a process for preparing oxcarbazepine of formula

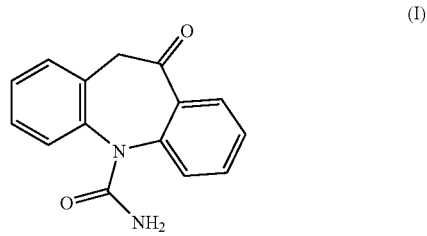

(I)

which includes:

a) the chlorocarbonylation reaction of the compound of formula

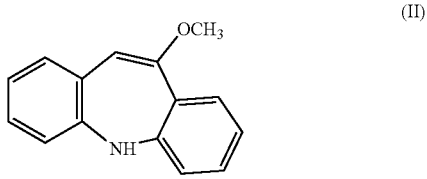

(II)

with triphosgene in the presence of a base, to give the compound of formula

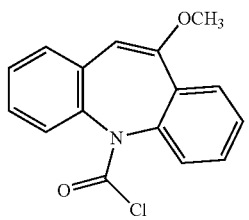

(III)

b) ammonolysis of the compound of formula III to give the compound of formula

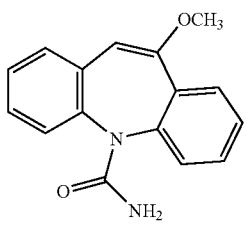

(IV)

and c) acid hydrolysis of the compound of formula IV to give oxcarbazepine I.

This process may be performed via the isolation and the optional purification of the individual intermediates of formulae II and III, or, preferably, by minimizing this procedure, i.e. working directly on the crude reaction product from the partially worked-up preceding step, as illustrated in the experimental section.

The starting compound of formula II of the process that is the subject of the present invention is commercially available.

The chlorocarbonylation step a) is performed with triphosgene in a molar ratio, relative to the compound of formula II, preferably of between 0.46:1 and 0.54:1 and more preferably at about 0.5:1, in the presence of a base, preferably an organic base and more preferably triethylamine, in a molar ratio relative to the compound of formula II of between 1.4:1 and 1.6:1 and preferably at about 1.5:1.

The reaction solvent is generally chosen from aromatic hydrocarbons, preferably toluene, and the reaction temperature is usually between 90 and 110° C.; preferably, the temperature at the start of dropwise addition of the triphosgene is greater than 90° C., to subsequently reach the reflux temperature of toluene during the dropwise addition. Preferably, once step a) is complete, the reaction medium is subjected to a minimum work-up and the residual crude product, obtained by evaporation, is used directly in the subsequent step b).

This ammonolysis step is generally performed with ammonia, preferably aqueous ammonia, in a suitable solvent, preferably an alcohol and more preferably methanol.

The subsequent deprotection step c) is preferably performed on the concentrate obtained directly from the preceding step, under acidic conditions, preferably with hydrochloric acid, in aqueous medium at a pH of between 0 and 2, preferably at about pH 1, and at a temperature above 50° C., preferably between 90 and 95° C.

The final product is preferably purified by crystallization, more preferably by crystallization from dimethylacetamide/methanol.

The overall yield for the present process is generally about 80%, i.e. appreciably greater than the yields for the similar processes described in the art.

The following examples are now given for the purpose of better illustrating the present invention without, however, limiting it.

EXPERIMENTAL SECTION

EXAMPLE 1

Preparation of 10-methoxy-5H-dibenzo[b,f]azepine-5-carboxamide (IV)

100 g (0.4479 mol) of 10-methoxy-5H-dibenz[b,f]azepine (II) are introduced into a round-bottomed flask, they are placed in suspension by adding 500 ml of toluene, 67.2 g (0.6641 mol) of triethylamine are added and the mixture is heated to 90° C. A solution consisting of 66 g of triphosgene (0.2224 mol) in 150 ml of toluene is then added dropwise over 40 minutes, while allowing the temperature to rise to 110° C.

Once the dropwise addition is complete, HPLC monitoring indicates that the reaction is complete. The reaction mixture is cooled to 80° C. and 300 ml of water are then added dropwise. After the dropwise addition, the internal temperature of the mixture is 60-65° C. The phases are separated at a temperature above 30-35° C. and the aqueous phase is removed.

The organic phase is evaporated to dryness under vacuum at about 40° C. and is then taken up in 125 ml of methanol. This solution is evaporated under vacuum at 40° C. and the residue is taken up again in 500 ml of methanol.

The solution is heated to 50° C., 300 ml of 28% aqueous ammonia (2.11 mol) are added dropwise to the homogeneous solution, and the mixture is stirred at 50° C. for 1 hour. HPLC monitoring after 1 hour indicates that the reaction is complete, and the solvent is partially distilled off at 40° C. under vacuum, down to a residual volume of about 400 ml. The solution at 25° C. becomes turbid due to precipitation of 10-methoxy-5H-dibenzo[b,f]azepine-5-carboxamide (IV), and the suspension thus formed is used without further purification in the following step.

EXAMPLE 2

Preparation of Oxcarbazepine (I)

600 ml of water are added to the round-bottomed flask containing the suspension of 10-methoxy-5H-dibenzo[b,f]azepine-5-carboxamide (IV) from Example 1, and about 12 g of 37% HCl are added dropwise to pH=1. The suspension is stirred at about 95° C. for 4 hours.

The mixture is cooled to 25° C. and about 14 g of 30% NaOH are added dropwise to bring the pH from 1.0 to 7.0-7.5. The reaction suspension is filtered at 25° C. and the cake is washed twice with water (2×100 ml), the filtration and washing waters then being removed. The cake is washed three times with methanol (3×100 ml) at 12-14° C. and the waters are then removed. The wet cake (160-170 g) is suspended in dimethylacetamide (400 ml) while heating at 110° C. until the solid has dissolved. The product is filtered off at a temperature above 80° C. (temperature of start of recrystallization). The filtrate is cooled to 60° C., 400 ml of methanol are then added to the suspension, and the resulting mixture is cooled first to 25° C. and then to 0-5° C. After 1 hour at 0-5° C., the cake is washed with 150 ml of methanol at 12-14° C. and the methanolic washing phase is removed. The cake is dried under vacuum at 40° C. for 6 hours.

| Weight: | about 80 g; |
|---|---|
| yield: | 70% (molar), 80% (w/w). |
| Purity (HPLC): | >99% (area %) |

The invention claimed is:

1. Process for preparing oxcarbazepine of formula (I)

which comprises:

a) reacting in a chlorocarbonylation reaction the compound of formula (II)

with triphosgene in the presence of a base, to give the compound of formula (III)

wherein said process results in an increased overall yield in comparison to comparable processes incorporating either phosgene or diphosgene.

2. The process of claim 1, which further comprises:

b) ammonolysis of the compound of formula to give the compound of formula (IV)

and c) deprotecting the compound of formula IV by acid hydrolysis to give oxcarbazepine of formula (I)

(I)

3. The process of claim 1, in which said chlorocarbonylation reaction a) is performed with triphosgene in a triphosgene molar ratio, relative to the compound of formula II, of between 0.46:1 and 0.54:1.

4. The process of claim 1, wherein the base is triethylamine, in a base molar ratio relative to the compound of formula II of between 1.4:1 and 1.6:1.

5. The process of claim 1, in which said chlorocarbonylation reaction a) is performed in toluene at a temperature of between 90 and 110° C.

6. The process of claim 2, in which the ammonolysis b) is performed with aqueous ammonia in methanol.

7. The process of claim 2, in which the deprotecting step c) is performed with hydrochloric acid in aqueous medium at a pH of about 1 and at a deprotecting temperature of between 90 and 95° C.

8. The process of claim 1, in which said chlorocarbonylation reaction a) is performed with triphosgene in a triphosgene molar ratio, relative to the compound of formula II, of about 0.5:1.

9. The process of claim 1, wherein the base is triethylamine, in a base molar ratio relative to the compound of formula II of about 0.5:1.

10. The process of claim 1, wherein
   (i) said chlorocarbonylation reaction a) is performed with a triphosgene molar ratio, relative to the compound of formula II, of between 0.46:1 and 0.54:1,
   (ii) the base is triethylamine, in a base molar ratio relative to the compound of formula II of between 1.4:1 and 1.6:1 and
   (iii) chlorocarbonylation reaction a) is performed in toluene.

11. The process of claim 1, wherein the overall yield is about 80%.

12. Process for preparing oxcarbazepine of formula

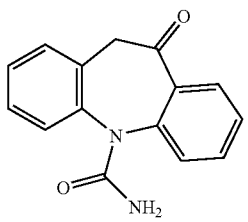

(I)

which comprises:
a) reacting in a chlorocarbonylation reaction the compound of formula

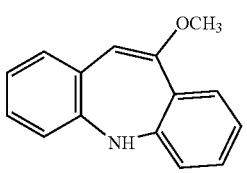

(II)

with triphosgene in the presence of a base, to give the compound of formula

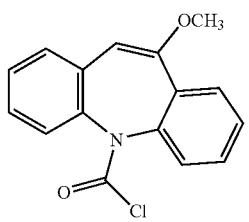

(III)

said process further comprising
b) ammonolysis of the compound of formula III to give the compound of formula

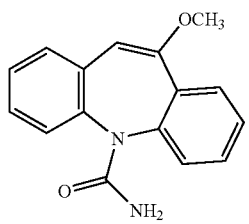

(IV)

and
c) deprotecting the compound of formula IV by acid hydrolysis to give oxcarbazepine of formula (I)

(I)

wherein said process results in an increased overall yield in comparison to comparable processes incorporating either phosgene or diphosgene,
and said deprotecting step c) is performed in an aqueous medium with hydrochloric acid at a temperature of between 90 and 95° C.

13. The process of claim 12, wherein said wherein said deprotecting step c) is performed at a pH ranging between 0 and 2.

* * * * *

UNITED STATES PATENT AND TRADEMARK OFFICE
CERTIFICATE OF CORRECTION

| | | |
|---|---|---|
| PATENT NO. | : 7,858,779 B2 | Page 1 of 1 |
| APPLICATION NO. | : 10/580145 | |
| DATED | : December 21, 2010 | |
| INVENTOR(S) | : Banfi et al. | |

It is certified that error appears in the above-identified patent and that said Letters Patent is hereby corrected as shown below:

Claims

Column 6
Claim 2, Line 3, insert --III-- immediately following ammonolysis of the compound of formula Signed and Sealed this
Eighth Day of February, 2011

David J. Kappos
*Director of the United States Patent and Trademark Office*